(12) United States Patent
Nilsson

(10) Patent No.: US 6,265,221 B1
(45) Date of Patent: Jul. 24, 2001

(54) DEVICE FOR TRAPPING AND ASSAYING C14 LABELLED CARBON DIOXIDE AND METHOD OF USE

(75) Inventor: Stefan Nilsson, Bromma (SE)

(73) Assignee: Noster System AB (SE)

( * ) Notice: Subject to any disclaimer, the term of this patent is extended or adjusted under 35 U.S.C. 154(b) by 0 days.

(21) Appl. No.: 09/319,492
(22) PCT Filed: Dec. 1, 1997
(86) PCT No.: PCT/SE97/02011
 § 371 Date: Jun. 7, 1999
 § 102(e) Date: Jun. 7, 1999
(87) PCT Pub. No.: WO98/26283
 PCT Pub. Date: Jun. 18, 1998

(30) Foreign Application Priority Data

Dec. 9, 1996 (SE) .................................................... 9604519

(51) Int. Cl.⁷ ...................................................... G01N 33/50
(52) U.S. Cl. ............................. 436/133; 422/83; 422/84; 422/88; 436/900; 430/30
(58) Field of Search ............................... 73/23.22; 422/58, 422/71, 80, 84, 85, 86, 88; 436/57, 58, 133, 169

(56) References Cited

U.S. PATENT DOCUMENTS

| | | | |
|---|---|---|---|
| 3,437,448 | * 4/1969 | Micska | 436/132 |
| 3,969,496 | * 7/1976 | Schrot | 250/303 |
| 4,564,021 | 1/1986 | Siegmann | 128/716 |
| 4,830,010 | 5/1989 | Marshall | 436/811 |
| 4,947,861 | 8/1990 | Hamilton | 128/719 |
| 5,124,129 | * 6/1992 | Riccitelli et al. | 422/56 |
| 5,468,451 | * 11/1995 | Gedeon | 422/58 |
| 5,719,052 | * 2/1998 | Ito et al. | 435/287.1 |
| 5,848,975 | * 12/1998 | Phillips | 600/532 |

FOREIGN PATENT DOCUMENTS

| | | | |
|---|---|---|---|
| 0253927 | * | 1/1988 | (EP) . |
| 0480177 | | 4/1992 | (EP) . |
| 9632062 | | 10/1996 | (WO) . |

OTHER PUBLICATIONS

B.J. Marshall, et al., *The American Journal of Gastroenterology*, vol. 86, No. 4, 1991, pp. 438–445.

* cited by examiner

Primary Examiner—Jill Warden
Assistant Examiner—Yelena G. Gakh
(74) Attorney, Agent, or Firm—Ostrolenk, Faber, Gerb & Soffen, LLP

(57) ABSTRACT

A device for use in trapping and assaying $^{14}CO_2$ in air exhaled by a person to which a $^{14}CO$ labelled compound has been administered, in particular $^{14}CO$ labelled urea, comprises first and second substantially flat oblong duct forming elements joined to each other at their edges except for one of their short edges and forming a duct between them. The first duct forming element includes a gas permeable matrix element for absorption of $CO_2$. The device is provided with indicator means for visual detection of $CO_2$ absorption and a film element of low β-radiation absorptivity interposed or interposable between the matrix element and a β-radiation measuring instrument. Also disclosed is a corresponding method.

20 Claims, 4 Drawing Sheets

DEVICE FOR TRAPPING AND ASSAYING C14 LABELLED CARBON DIOXIDE AND METHOD OF USE

FIELD OF THE INVENTION

Figure 1:
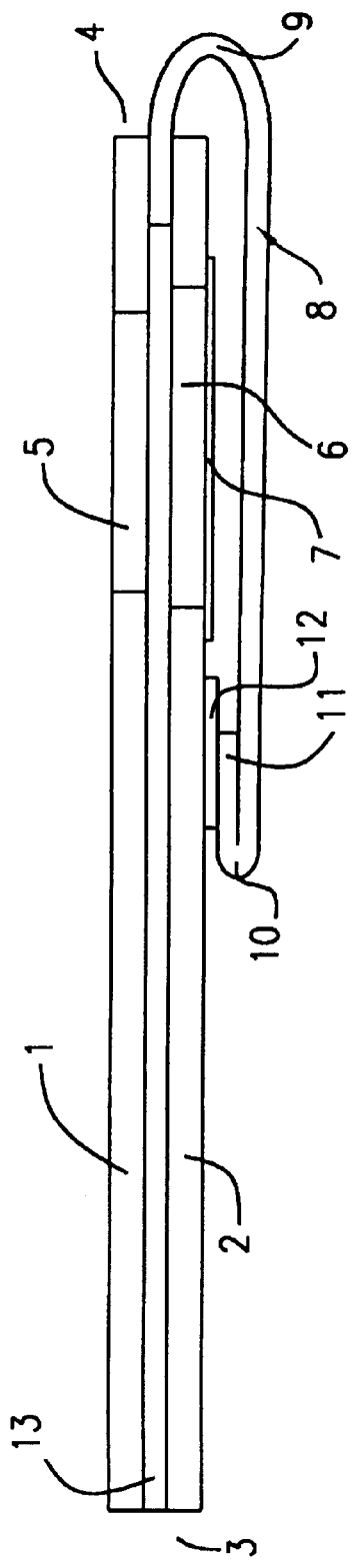

The present invention relates to a device for use in trapping and assaying $^{14}CO_2$ in air exhaled by a person to which $^{14}C$ labelled compound has been administered, in particular $^{14}C$ labelled urea, and a corresponding method.

BACKGROUND OF THE INVENTION

Certain conditions and diseases can be indicated by analyzing exhaled air. For instance, air exhaled by persons suspected to be infected by the pathogenic bacteria *Helicobacter pylori* is analyzed by a variety of methods. According to one such method used clinically for a number of years, the patient is made to swallow an isotope-labelled urea preparation, in particular a preparation containing $^{14}C$ or $^{14}C$ labelled urea. *Helicobacter pylori* present in the gastrointestinal tract produces enzymes degrading the urea to ammonia/carbon dioxide. The gastro-intestinally formed carbon dioxide is transported to the lungs through the normal physiology of the body and exhaled together with other carbon dioxide formed by the body. The exhaled carbon dioxide is trapped by a suitable liquid, for instance, aqueous sodium hydroxide, which is examined with the aid of appropriate measuring instruments, for instance scintillation counters for detecting radioactive decay of $^{14}C$.

The methods known in the art are relatively complicated and time consuming, and require the use of expensive and bulky apparatus. The provision of simple and cheap methods for use in decentralised health care has still not been adequately solved. There is thus a need for such methods and corresponding devices.

OBJECTS OF THE INVENTION

An object of the present invention is to provide a simple device for use in trapping and assaying of $^{14}C$ in air exhaled by a person under clinical investigation for a disease characterised by an increased metabolic rate for the transformation of $^{14}C$ labelled organic compounds, for instance of $^{14}C$ urea, to $^{14}CO_2$.

Another object of the present invention is to provide a method for clinical use of this device.

Further objects of the invention will become apparent from the following description of the invention and the appended claims.

SUMMARY OF THE INVENTION

According to the present invention is disclosed a device of the aforementioned kind comprising first and second substantially flat oblong duct forming elements joined to each other at their respective edges except for one of their short edges and forming a duct between them, the first duct forming element including a gas permeable matrix element for absorption of $CO_2$, the device being provided with indicator means for detection of $CO_2$ absorption and a film element of low β-radiation absorptivity interposed or interposable between the matrix element and a β-radiation measuring instrument.

It is preferred for the film element to have a thickness of less than 0.05 mm, more preferably of less than 0.015 mm.

It is preferred for the matrix element to comprise a matrix, an absorbant for carbon dioxide, and an indicator for indication of carbon dioxide absorption.

It is preferred for the absorbant for carbon dioxide to comprise a strong base such as lithium hydroxide, sodium hydroxide, and calcium hydroxide.

It is preferred for the matrix element to be of such design and have such carbon dioxide absorption capacity as to become saturated with carbon dioxide within about one to two minutes by passage of the air exhaled by an adult person. The proper load of carbon-dioxide absorbant can be easily determined by experiment for matrix elements of various size and physical characteristics as well as chemical properties.

It is preferred for the indicator to be a pH indicator, preferably a pH indicator for visual indication of a pH change above pH 10. It is particularly preferred for the indicator to be selected form colour indicators changing from an uncoloured form at high pH to a coloured form at lower pH. Particularly preferred is the indicator phenolphthalein. Also preferred is the indicator tropaeolin.

The film forming element is advantageously provided with perforations to allow exhaled air to pass through it. The diameter of such perforations is preferably less than 2 mm, more preferably less than 1 mm, most preferably less than 0.5 mm. To balance the air flow through the device, perforations can also be arranged in one or both of the duct forming elements.

According to a first aspect of the invention it is preferred for the second duct forming element to have a through opening disposed opposite to the matrix element and being covered by the film element, the device preferably comprising a flexible flap secured at the closed short end and having a length sufficient for covering, in a first position, the through opening of the second duct forming element and, in a second position, the matrix element of the first duct forming element. The flap should be of a white reflective material. In its first position, the flap enhances the visibility of colour change by forming a standard reflective background to the matrix element. In its second position, it covers the now humid or wet matrix element and provides for hygienic handling of the device. It is preferred for the flap to be removable fixed at the second duct forming element in said first position. It is also preferred for the flap to be adhesively fixable to the first duct forming element in said second position. The means for adhesive fixation of the flap to the first duct forming element preferably are comprised by the means for its removable fixation at the second duct element.

According to a second aspect of the invention, it is preferred for the film element to have the form of a flexible flap secured at the closed short end and having a length sufficient for covering the matrix element of the first duct forming element. It is preferred for the film flap to be removably fixable at the second duct forming element.

According to a third aspect of the invention, the indicator means is disposed separate from the matrix element. The indicator means preferably comprises a pH indicator, in particular a pH indicator indicating by changed of colour a pH change above pH 10 and being disposed in a second matrix element for absorption of $CO_2$.

The duct forming elements can be made in one piece, for instance by appropriate punching, folding and sealing of a piece of cardboard. They may also be joined at their edges partially or wholly by intermediate elements. The design of the device according to the invention provides for measurement of β-radiation from $^{14}C$ by comparatively inexpensive equipment, in particular a Geiger-Müller counter into a measuring cavity of which the device may be inserted.

According to the present invention is disclosed a method for trapping and assaying $^{14}C$ exhaled by a person under investigation for a disease or condition characterised by increased enzymic activity in the gastro-intestinal tract leading to carbon dioxide formation from an enzymatically degradable agent administered to said person, comprising:

making said person exhale into the one open short end of a device comprising first and second substantially flat oblong duct forming elements joined to each other at their respective edges except for said short end, the first duct forming element having an air-permeable matrix element covered by or coverable by a protective element with low β-radiation absorptivity, the matrix element including a carbon dioxide absorbant, the device further comprising indicator means for visual detection of $CO_2$ uptake by change of colour, observing the indicator means to detect a colour change, stopping exhalation into the device upon observation of the colour change, optionally covering the matrix element with a protective element, measuring β-radiation originating form the matrix element for a period of time by bringing the device into contact with an apparatus for β-radiation measurement, comparing the number of registered decay events with that obtained from healthy persons.

Apparatus for detection of $^{14}C$ radiation include in particular Geiger-Müller counters. An increase of β-radiating activity over the background value found in healthy persons indicates the presence of enzymic activity of the aforementioned kind, and thus a condition deviating from what is considered normal.

Figure 2:
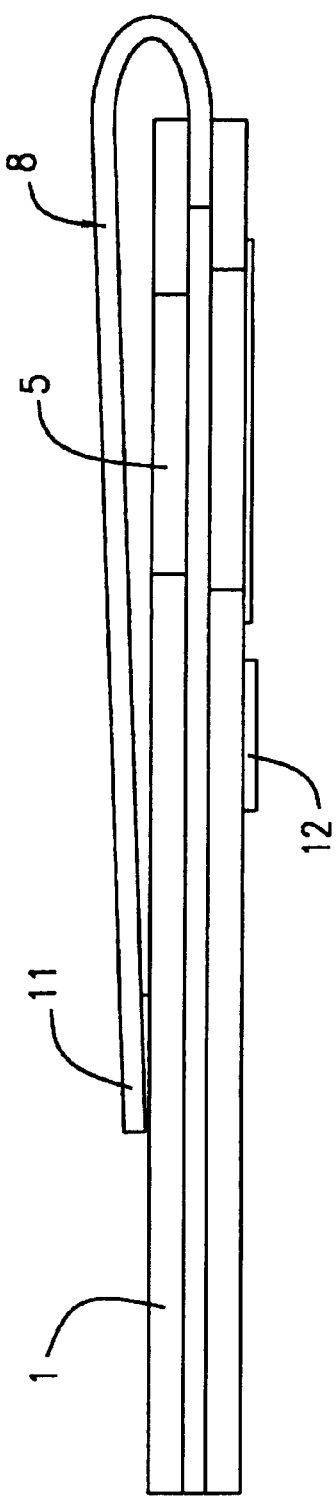
Figure 3:
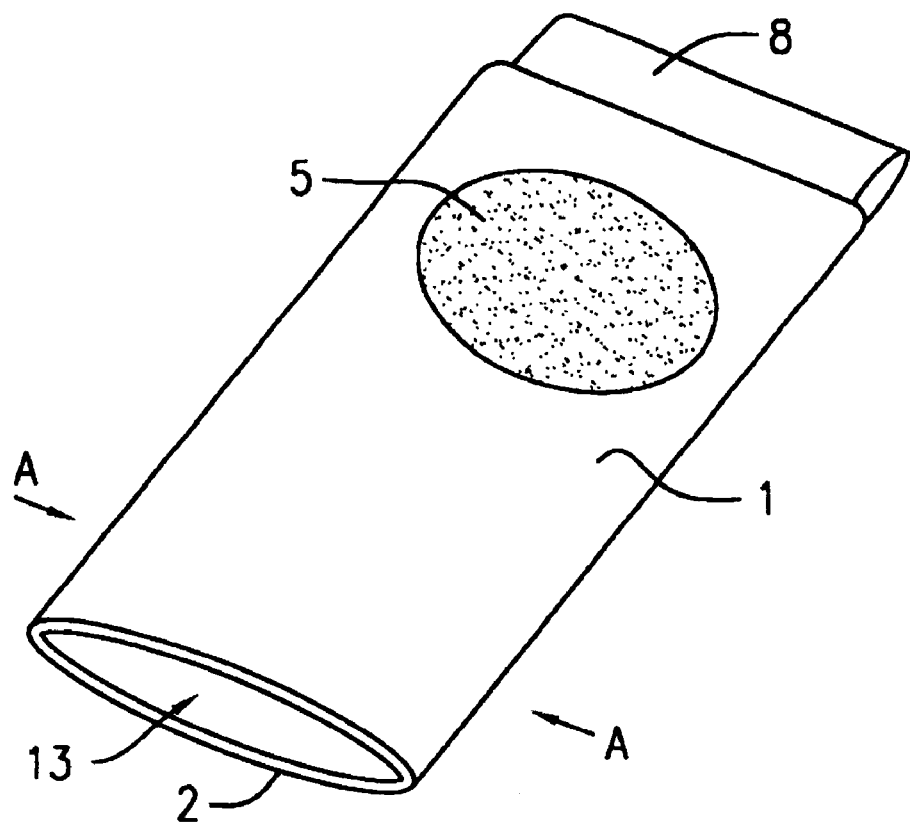
Figure 4:
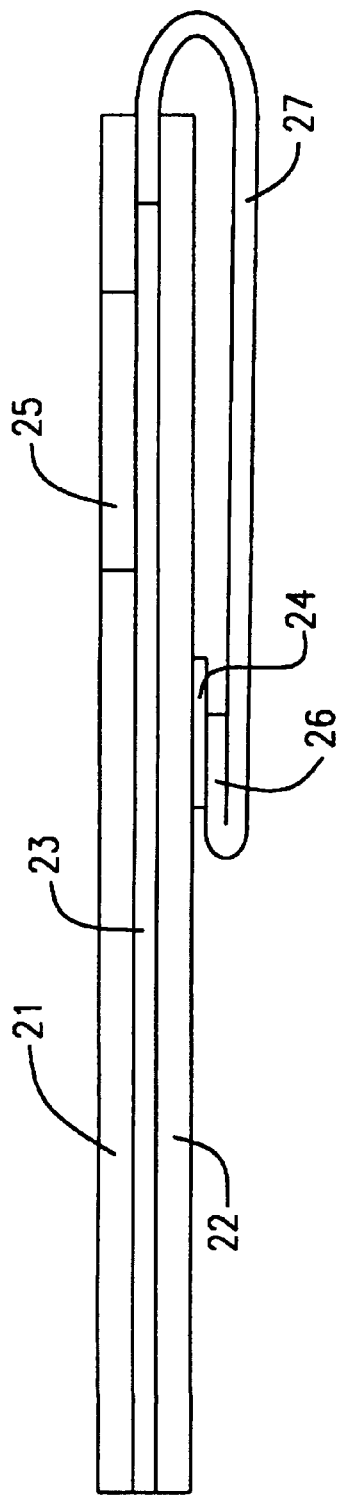
Figure 5:
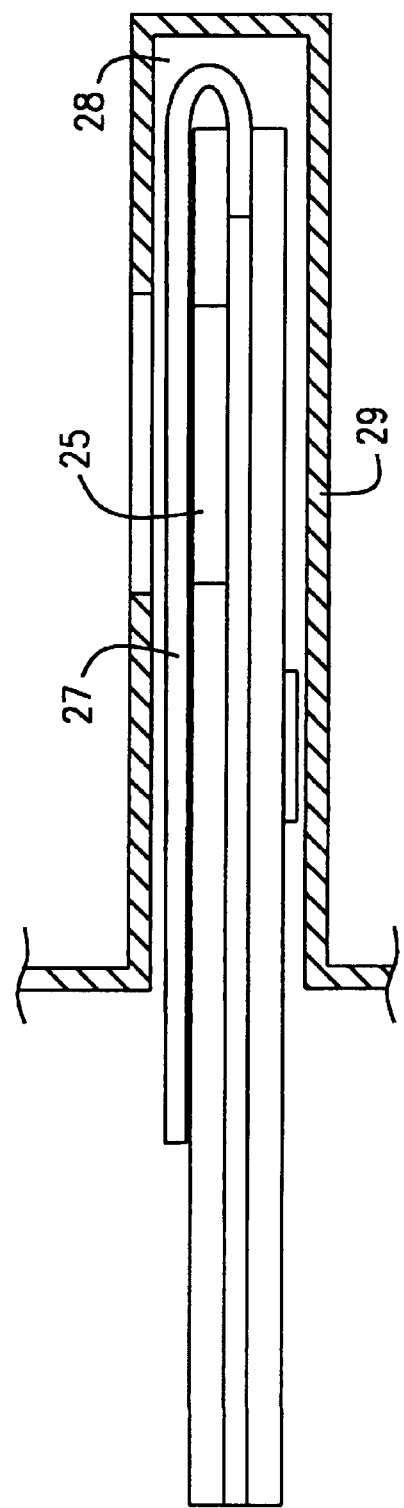

In the following, the invention will be explained in detail by reference to preferred embodiments which however should not be understood to limit the scope of invention and which are illustrated in the attached drawing, showing in FIG. 1 a first embodiment of the invention, in a longitudinal section, the transverse dimensions being greatly exaggerated for the sake of clarity, with the flap in a first position;

FIG. 2 the device of FIG. 1 in the same representation, with the flap in a second position;

FIG. 3 the device of FIG. 1, in a perspective view and in a slightly deformed condition ready for exhalation;

FIG. 4 a second embodiment of the invention, in a view corresponding to that of the first embodiment in FIGS. 1 and 2, with the flap in a first position;

FIG. 5 the device of FIG. 4 in the same representation, inserted into the measuring cavity of a Geiger-Müller tube and with the flap in a second position;

FIGS. 6a–d a third embodiment of the invention, in a view corresponding to that of the first embodiment in FIGS. 1 and 2, before and after use, in a perspective view (6a–c) and sectioned (6d).

The device according to the invention shown in FIGS. 1–3 comprises a thin-walled first duct forming element 1 and a thin-walled second duct forming element 2 of rectangular and congruent shape. Elements 1, 2 are disposed in a superposed position and joined at their respective edges except for the edges at one short end 3, thereby forming a duct 13. The preferred material for elements 1 and 2 is cardboard; it is also possible, for instance, to use a plastic material for one or both of them.

The first duct forming element 1 has a through opening provided with a gas permeable matrix element 5 for absorption of $CO_2$. The second duct forming element 2 has a through opening 6 disposed opposite to the matrix element 5 and covered by a film 7 glued to element 2 at its edges. The film 7 is made of a low β-radiation absorbing material, such as a poly(ethylene glycol-terephthalate) polyester made by Du Pont sold under the trademark Mylar®, and has a thickness of less than 0.05 mm, preferably less than 0.015 mm.

The matrix element 5 has the form of a flat cylinder of a size matching the circular opening 6. It may be as thin as paper and should have low air flow resistance. It may be fixed in the opening of the first duct forming element of corresponding size by gluing or pressure. In principle the first duct forming element and the matrix element may be made in one piece from an open matrix structure such as non-woven impregnated with a second material, for instance a polymer, in areas intended to be impenetrable to air, whereas the area corresponding to the matrix element 5 is left unimpregnated and is loaded with a carbon dioxide absorbent and an indicator. A wide range of materials can be used for the matrix element, in particular non-woven matrixes based on cellulose and cellulose derivatives, synthetic polymers such as polystyrene and polyether, glass or mineral wool, finely dispersed carbon, alumina or silica in an air permeable cover, etc. It is important for the matrix element to have a large surface covered with a thin layer of the agent or combination of agents for absorption of carbon dioxide from the exhaled air. By experiment, the filter tissue DUTEXIM™ 4106 or 4108 of Tharreau Ind., Chemillé, France was found particularly useful.

A wide variety of agents for absorption of carbon dioxide are known in the art. Particularly useful are the alkali metal hydroxides, in particular lithium hydroxide, sodium hydroxide, and their mixtures. Also useful are, for instance, other basic oxides, such as calcium hydroxide, and high capacity ion exchange resins (forming their own support). Further useful agents comprise non-volatile amines, in particular high molecular amines such as chitosan. Application of the absorption agents of the invention may be enhanced by surfactants, such as alkyl and aryl sulphonates. Also incorporated may be agents promoting humidification of the absorption agent, that is, uptake of water from the exhaled air partially or wholly dissolving the absorption agent or make it swell, which process enhances the uptake of carbon dioxide. Humidification promoting agents include lithium chloride and magnesium chloride. The absorption agent is applied by soaking the matrix in an aqueous or alcoholic solution of the agent. A load of 350 of aqueous 1.2 M LiOH per $m^2$ of filter tissue was found satisfactory by experiment.

The saturation of the carbon dioxide absorbing agent of the matrix element is indicated by a change in colour of pH indicator added to the carbon dioxide absorbing agent. It is not necessary to saturate the absorbent with carbon dioxide. Absorption thus may conveniently be stopped at a pH above 10. Particularly useful is phenolphthalein as pH indicator in the form of its colourless trianionic form (for instance, trisodium salt) which changes to its red dianionic form already at a pH above 12. Since the change is from colourless to red, it is particularly easy to observe. Other useful indicators are, for instance, 5,5'-indigodisulfonic acid di-sodium salt which changes from yellow to blue (colour change on lowering of pH) at pH 13–11.4, Alizarin Yellow R which changes from red to yellow at pH 12.0–10.1, and 2,4,6-trinitrotoluene which changes from orange to colourless at pH 13.0–11.5. The indicator tropaeolin (colour change yellow/orange at a pH of about 12–13) was found experimentally to be particularly useful. A load of 350 ml of a 0.1% solution of tropaeolin per $m^2$ of filter tissue was found satisfactory by experiment.

At its second short end 4, the device carries a flexible rectangular flap 8, for instance of white paper, adhesively secured between the duct forming elements 1, 2; its length suffices for covering, in a first position, the through opening 6 of the second duct forming element 2 and, in a second position, the matrix element 5 of the first duct forming element 1. The flap 8 is folded twice to make a 180° loop in front of the second device end 4, then extending parallel with and covering the second duct forming element 2 to which it is fasted at its free end portion 11 after having made a second 180° loop 10 (in the same sense as the first loop 9). The adhesive fastening of end portion 11 to the second duct forming element 2 is comparatively weak to allow it being released after loading of the device with carbon dioxide. For that reason, a release patch or layer 12 of appropriate material, for instance a hydrophobic smooth material such as used a backing material for address labels, is applied to the outside of duct forming element 2.

In its first position, the flap 8 enhances end point detection by providing a white reflective background to matrix element 5 which is observed at its surface coplanar with that of the first duct element 1. In its second position, the flap 8 protects the now loaded and wet matrix element 5.

The device of FIGS. 1–3 is essentially flat and easily housed in a sealed envelope to exclude air and humidity. The envelope, for instance of polythylene film, is opened prior to use, at which time it may be advisable to place the device for a short period in a high humidity chamber for equilibration to promote $CO_2$ uptake on exhalation. It is also possible to dispense water to the matrix element prior to use, for instance by dropping water on it with a pipette.

For use, the duct 13 opening at short end 3 forms a simple mouthpiece which can be widened by forcing the long side edges of the device against each other, as indicated by arrows A in FIG. 3 where duct elements 1 and 2 are shown in a slightly deformed condition. The person under investigation then exhales air through the duct 13 and matrix element 5 until a colour change is visible at the outside of matrix element 5. By having duct element 1 face upwards during exhalation the exhaling person can himself or herself observe the colour change and stop the procedure at the right moment. The flap 8 is released from its first position, turned around, and fixed to the first duct element 1 while protecting the now humid or even wet matrix element 5. For measurement of β-radiation the device is held with its window film 7 against the window of a Geiger-Müller counter or other β-radiation detecting device for a measured period of time, or is inserted into the measuring cavity of such a device. The recorded activity is compared to the activity mean recorded for healthy persons. A statistically significant deviation from that mean is considered as indication of infection.

The second embodiment of the invention illustrated in FIGS. 4 and 5 comprises a thin-walled first duct forming element 21 and a thin-walled second duct forming element 22 of rectangular and congruent shape disposed in a superposed position and joined at their respective edges except for the edges at one short end, thereby forming a duct 23. The first duct forming element 21 has a through opening provided with a gas permeable matrix element 25 for absorption of $CO_2$. This second embodiment of the invention differs from the first embodiment shown in FIGS. 1–2 by the second duct forming element 22 not having a through opening disposed opposite to the matrix element 25 and by having a flap 27 secured at its closed short end made of a material having a low β-radiation absorption coefficient such as, for instance, Mylar, releaseably secured at its folded-over free end 26 to a low adhesion patch 24 in a first position shown in FIG. 4.

The second embodiment of the invention is used for $CO_2$ absorption in manner corresponding to that disclosed above for the first embodiment, the white area of second duct forming element 22 opposite to the matrix element 25 assuming the reflecting function of flap 8 of the first embodiment. Upon the colour change of the indicator on matrix element 25, end 26 of flap 27 is peeled off from patch 24, the entire flap 27 is folded over to face the first duct forming element 21 so as to cover the now humid matrix element 25; thereupon the device is inserted in the sample cavity 28 of a Geiger-Müller tube. Decay events of $^{14}C$ trapped by the matrix element 25 result in β-particles travelling through the radiation-transparent flap 27 and impinging on the Geiger-Müller tube wall 29, thereby eliciting a recordable electric discharge. It is not necessary for the free end portion 26 of flap 27 to be fastened at the first tube forming element, in particular if the measurement is carried out directly upon $CO_2$ sampling.

Figure 6A:
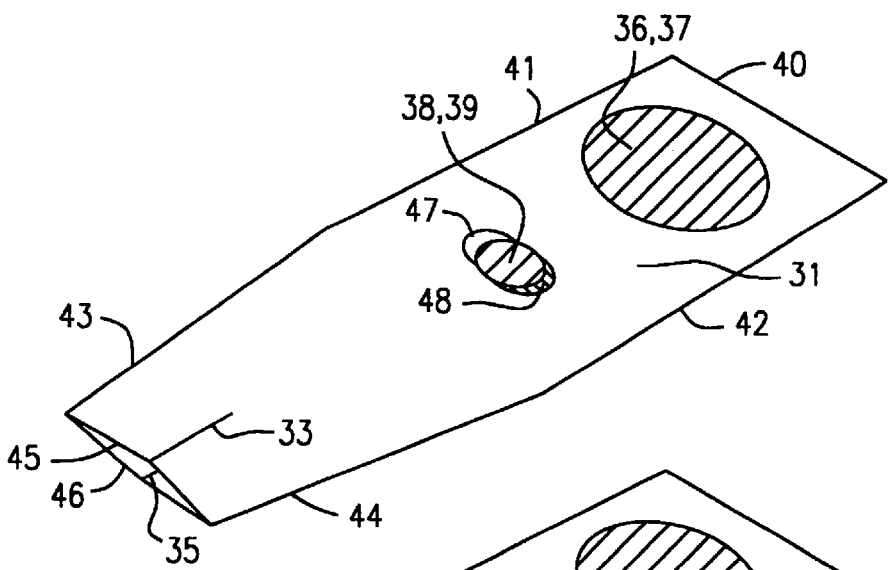
Figure 6B:
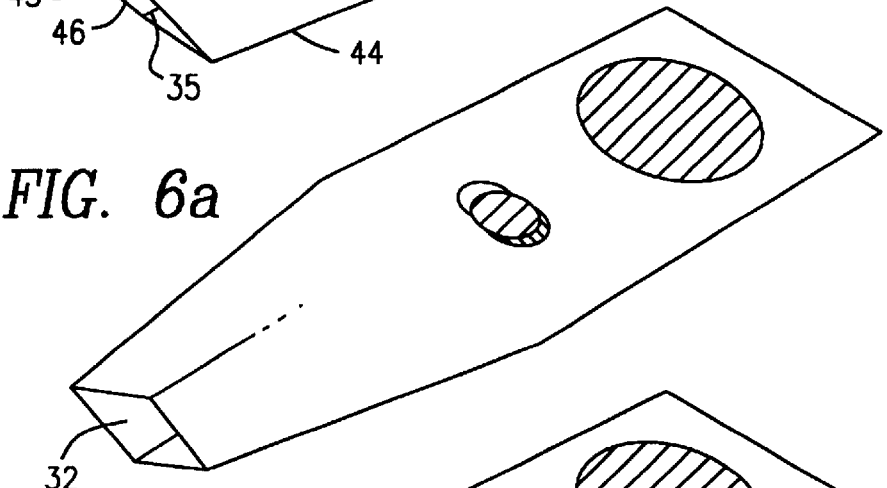
Figure 6C:
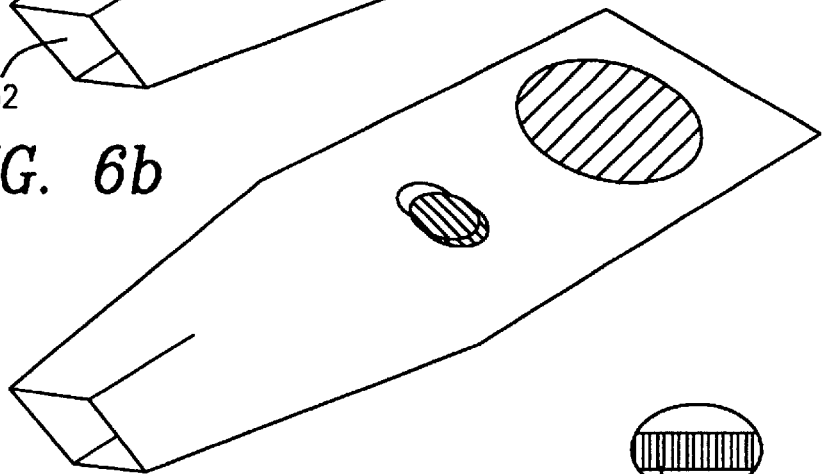
Figure 6D:
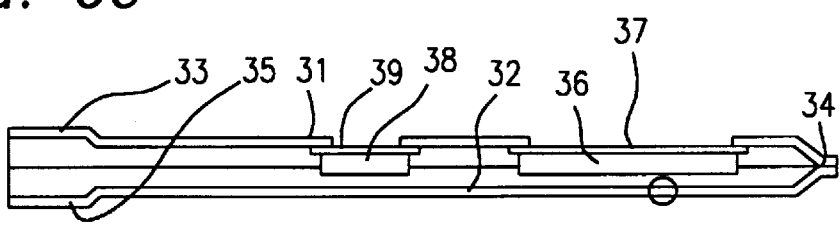

The third embodiment shown in FIG. 6d in section and in FIG. 6a rough perspective view is similar to the other embodiments but lacks, i.a., their flap. It is particularly suited for on-site measurement of $^{14}C$. Its first 31 and second 32 duct forming elements are thin sheets of polyester having identical contour. They are joined at their periphery by jig-welding in superimposed position, thereby forming a tubiform element sealed at its lateral 41, 42, 43, 44 and back 40 edges. The front edges 45, 46, in the direction of which the lateral edges converge by edge portions 43, 44, are kept separate to pre-form a mouth piece. The first duct-forming element 31 has two circular through openings, a larger one near the back edge 40 and a smaller one located between the larger opening and the mouthpiece. On its inside, the first (larger) opening is covered by a first film disk 37 of a material with low β-radiation absorption. The first film disk 37 has a diameter slightly larger than that of the larger opening to make it overlap with the first film 31 forming element to which it is glued at its periphery. Beneath the first film disk 37 is located a first matrix disk 36 of a size somewhat larger than the opening but somewhat smaller than the first film disk 37 to which it is glued at its periphery. The second (smaller) opening is provided with correspondingly arranged second film 39 and second matrix 38 disks; the second film disk 39 must be of a transparent material but not necessarily of one that has low β-radiation absorptivity. The matrix disks 36, 38 are of non-woven polyester. The first matrix disk 38 is loaded with lithium hydroxide whereas the second matrix disk is loaded with lithium hydroxide+pH-indicator (tropaeolin, for instance); in respect of lithium hydroxide (or any other strong base, if used) the disks are carrying comparable loads. The matrix disks are loaded with the chemicals by spraying with their aqueous or alcoholic solutions and thorough drying in a carbon dioxide-free atmosphere.

Flow of exhaled air through various parts of the third embodiments is provided for by arranging tiny passages through them. In FIG. 6 such passages 49 are only shown by exemplification in a portion of the second duct forming element 32 disposed opposite to the first matrix disk 36. Similar passages or holes are also provided in the first 37 and second 39 film disks. They can be made, for instance, by punching the respective material with an array of needles arranged, for instance, in the form of a brush. Their diameter, number, and location can be easily determined by experiment so as to provide for proper air flow distribution and resistance.

FIG. 6a shows the third embodiment prior to use. It is provided to the physician/user in a sealed, gas-tight envelope of plastic material (not shown) to protect it from carbon dioxide and moisture. Folding notches 33, 35 extending for a few centimetres from the centre of front edges 45, 46, respectively, in the direction of back edge 40 provide for easy formation of a mouthpiece by application of a slight pressure against lateral edges 43, 44. FIG. 6b shows the third embodiment ready for use with a fully formed mouthpiece.

When air is exhaled into the mouthpiece, it will flow, in part, through the matrix disks 36 and 38 and will then pass through the film disks 37 and 39 to leave the device through the first and second openings in the first duct forming element 31. The remaining air will pass through holes 49 arranged in the wall of the second duct forming element. Upon saturation of the lithium hydroxide in the second matrix disk with carbon dioxide, the pH indicator changes its colour (FIG. 6c). This indicates that the lithium hydroxide in the first matrix disk will also be saturated with carbon dioxide. The transparent second film disk 39 enables the person performing the test observe the colour change by comparison with coloured fields 47 (unsaturated condition) and 48 (saturated condition) printed on the outside of the first duct forming element 31 and extending from the periphery of the second opening.

What is claimed is:

1. A device for use in trapping and assaying $^{14}CO_2$ in air exhaled by a person to which a $^{14}C$ labelled compound has been administered, comprising first and second substantially flat oblong duct forming elements having long and short edges joined to each other at their respective edges except for one of their short edges and forming a duct between them, the first duct forming element including a gas permeable matrix element for absorption of $CO_2$, the device being provided with an indicator for detection of $CO_2$ absorption and a film element of low β-radiation absorptivity interposed or interposable between the matrix element and a β-radiation measuring instrument.

2. The device of claim 1, wherein the film element has a thickness of less than 0.5 mm.

3. The device of claim 2, wherein the matrix element comprises a matrix and an absorbent for carbon dioxide.

4. The device of claim 3, wherein the absorbant for carbon dioxide comprises a strong base.

5. The device of claim 4, wherein the base is selected from the group consisting of lithium hydroxide, sodium hydroxide, calcium hydroxide and their mixtures.

6. The device of claim 1 wherein the matrix element is of such design and has such carbon dioxide absorption capacity as to become saturated with carbon dioxide within from about one to two minutes by passage of the air exhaled by an adult person.

7. The device of claim 1, wherein the indicator comprises a pH indicator.

8. The device of claim 1 wherein the second duct forming element has a through opening disposed opposite to the matrix element covered by the film element.

9. The device of claim 8, comprising a flexible flap secured at a closed short end and having a length sufficient for covering, in a first position, the through opening of the second duct forming element and, in a second position, the matrix element of the first duct forming element.

10. The device of claim 1, wherein the film element has a form of a flexible flap secured at the closed short end and having a length sufficient for covering the matrix element of the first duct forming element.

11. The device of claim 1, wherein the indicator is comprised by the matrix element.

12. The device of claim 1, wherein the indicator is disposed separate from the matrix element.

13. The device of claim 12, wherein the indicator comprises a pH indicator disposed in a second matrix element for absorption of $CO_2$.

14. The device of claim 1, wherein the film forming element is provided with perforations.

15. A method for trapping and assaying $^{14}C$ exhaled by a person under investigation for a disease or condition characterised by increased enzymic activity in the gastrointestinal tract leading to carbon dioxide formation from an enzymatically degradable agent administered to said person, comprising:

making said person exhale into an open short end of a device comprising first and second substantially flat oblong duct forming elements joined to each other at their respective edges except for said short end, the first duct forming element having an air-permeable matrix element covered by or coverable by a protective element with low β-radiation absorptivity, the matrix element including a carbon dioxide absorbant, the device further comprising an indicator for visual detection of $CO_2$ uptake by change of colour;

observing the indicator to detect a colour change, and stopping exhalation into the device upon observation of such change;

optionally covering the matrix element with said protective element;

measuring β-radiation originating from the matrix element for a period of time by bringing the device into contact with an apparatus for β-radiation measurement; and comparing the number of registered decay events with that obtained from healthy persons.

16. The device of claim 5, wherein the film element has a thickness of less than 0.015 mm.

17. The device of claim 16, wherein the indicator comprises a pH indicator.

18. The device of claim 17, wherein the indicator comprises a pH indicator adapted to indicate a pH change above pH 10 by change of color.

19. The device of claim 1, wherein the film element has a thickness of less than 0.05 mm.

20. The device of claim 1, wherein the indicator comprises a pH indicator.

* * * * *